United States Patent
Wolford et al.

(10) Patent No.: US 11,033,282 B2
(45) Date of Patent: Jun. 15, 2021

(54) ACETABULAR/PATELLAR/GLENOID/CALCAR REAMER CUTTING TOOTH ARRANGMENT WITH DEPTH-OF-CUT CONTROL FEATURE

(71) Applicant: Symmetry Medical Manufacturing, Inc., Warsaw, IN (US)

(72) Inventors: Todd A. Wolford, Goshen, IN (US); Mark A. Nordman, Burket, IN (US); Ray Hathaway, Pierceton, IN (US)

(73) Assignee: Symmetry Medical Manufacturing, Inc., Warsaw, IN (US)

( * ) Notice: Subject to any disclaimer, the term of this patent is extended or adjusted under 35 U.S.C. 154(b) by 304 days.

(21) Appl. No.: 16/280,328

(22) Filed: Feb. 20, 2019

(65) Prior Publication Data
US 2019/0254686 A1  Aug. 22, 2019

Related U.S. Application Data

(60) Provisional application No. 62/633,854, filed on Feb. 22, 2018.

(51) Int. Cl.
*A61B 17/00* (2006.01)
*A61B 17/16* (2006.01)
*A61L 31/02* (2006.01)

(52) U.S. Cl.
CPC ...... *A61B 17/1666* (2013.01); *A61B 17/1668* (2013.01); *A61B 17/1677* (2013.01); *A61B 17/1684* (2013.01); *A61B 17/1686* (2013.01); *A61L 31/022* (2013.01)

(58) Field of Classification Search
CPC combination set(s) only.
See application file for complete search history.

(56) References Cited

U.S. PATENT DOCUMENTS

2013/0245628 A1* 9/2013 Sidebotham ........... A61B 17/16
606/80

\* cited by examiner

*Primary Examiner* — Sameh R Boles
(74) *Attorney, Agent, or Firm* — Taylor IP, P.C.

(57) ABSTRACT

An orthopaedic reamer includes a shell and a cutting tooth arrangement formed in the shell. The cutting tooth arrangement includes a cutting tooth having a predefined profile with a cutting edge having a cutting depth, and a depth-of-cut feature positioned forward of the cutting tooth, relative to a direction of movement of the shell at the location of the cutting tooth. The depth-of-cut feature has a control depth which controls a cutting depth of the cutting tooth during surgery.

10 Claims, 2 Drawing Sheets

ACETABULAR/PATELLAR/GLENOID/CALCAR REAMER CUTTING TOOTH ARRANGMENT WITH DEPTH-OF-CUT CONTROL FEATURE

CROSS REFERENCE TO RELATED APPLICATIONS

This is a non-provisional application based upon U.S. provisional patent application Ser. No. 62/633,854, entitled "ACETABULAR/PATELLAR/GLENOID/CALCAR REAMER CUTTING TOOTH ARRANGEMENT WITH DEPTH-OF-CUT CONTROL FEATURE", filed Feb. 22, 2018, which is incorporated herein by reference.

BACKGROUND OF THE INVENTION

1. Field of the Invention

The present invention relates to orthopaedic reamers, and, more particularly, to cutting teeth formed in such reamers.

2. Description of the Related Art

An acetabular reamer is used in hip replacement surgery to cut the acetabulum to the correct size to accept an implant. A patella reamer is used to cut the dome at the posterior of the patella to receive an implant. The glenoid reamer is used to prepare the shoulder joint to accept an implant. The calcar reamer is used to cut the calcar of the femoral bone to accept an implant. For a successful surgical outcome it is important that the reamer be sharp and at the same time be not overly aggressive such that it is hard for the surgeon to control the cut.

For the sake of simplicity, acetabular, glenoid, calcar, and patella reamers will hereafter be collectively referred to as reamers.

What is needed in the art are orthopaedic reamers that are sufficiently sharp without being overly aggressive.

SUMMARY OF THE INVENTION

Exemplary embodiments disclosed herein provide orthopaedic reamers with a cutting tooth arrangement that includes a cutting tooth and a depth-of-cut feature having a control depth which controls a cutting depth of the cutting tooth.

In some exemplary embodiments provided in accordance with the present invention, an orthopaedic reamer includes a shell and a cutting tooth arrangement formed in the shell. The cutting tooth arrangement includes a cutting tooth having a predefined profile with a cutting edge having a cutting depth, and a depth-of-cut feature positioned forward of the cutting tooth, relative to a direction of movement of the shell at the location of the cutting tooth. The depth-of-cut feature has a control depth which controls a cutting depth of the cutting tooth during surgery.

One possible advantage that may be realized by exemplary embodiments disclosed herein is the cutting tooth and the depth-of-cut feature may be easily adjusted to provide a surgeon's preferred cutting characteristics for the reamer.

Another possible advantage that may be realized by exemplary embodiments disclosed herein is the aggressiveness of the reamer can be controlled by adjusting the control depth.

BRIEF DESCRIPTION OF THE DRAWINGS

The above-mentioned and other features and advantages of this invention, and the manner of attaining them, will become more apparent and the invention will be better understood by reference to the following description of an embodiments of the invention taken in conjunction with the accompanying drawings, wherein.

Corresponding reference characters indicate corresponding parts throughout the several views. The exemplification set out herein illustrates an embodiment of the invention, and such exemplification is not to be construed as limiting the scope of the invention in any manner.

DETAILED DESCRIPTION OF THE INVENTION

Figure 1:
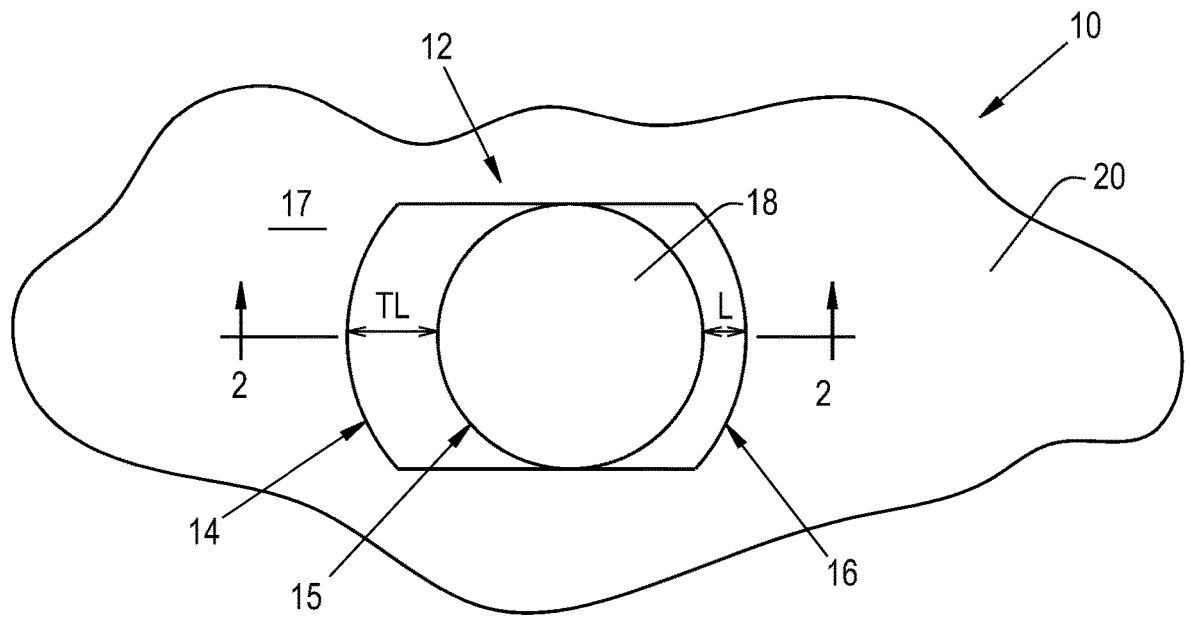
FIG. 1 is a plan view of a portion of a reamer, illustrating an embodiment of a cutting tooth arrangement of the present invention.
Figure 2:
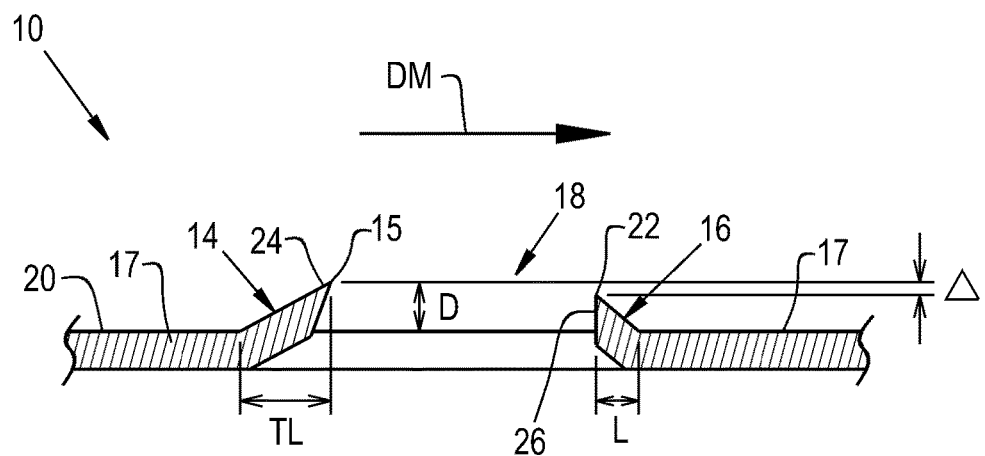
FIG. 2 is a sectional view taken along section line 2-2 in FIG. 1.
Figure 3:
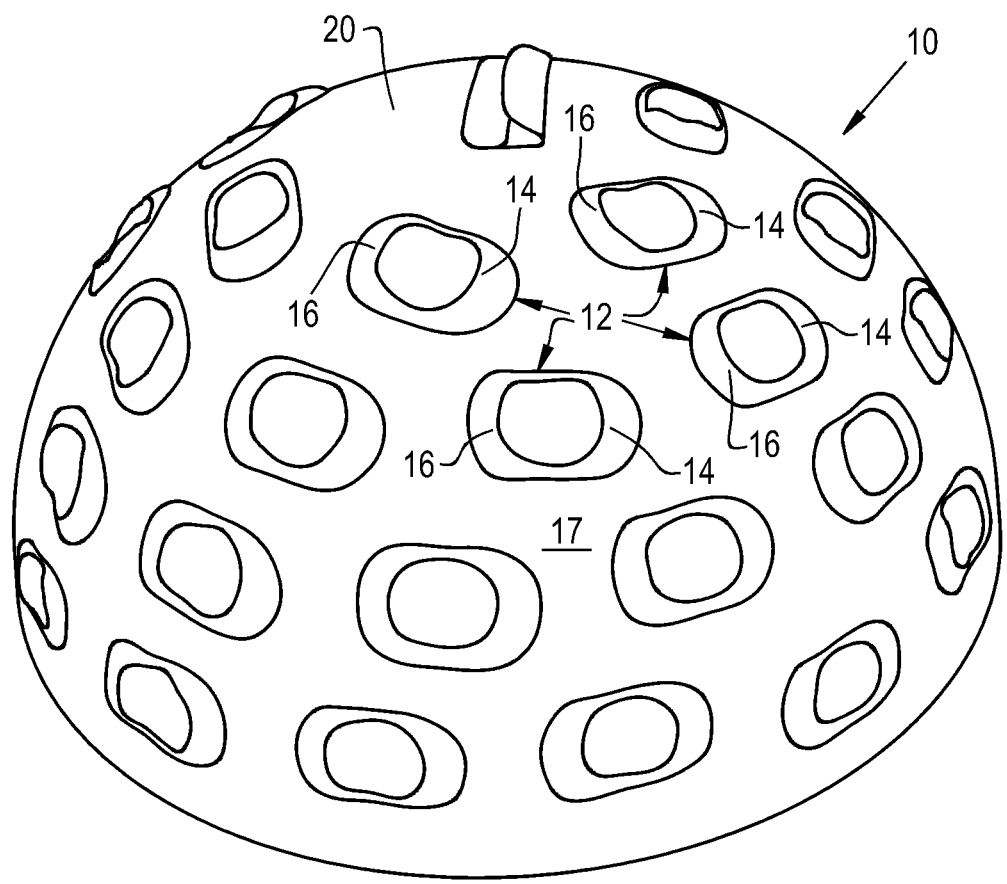
FIG. 3 is a perspective view of the reamer illustrated in FIGS. 1-2.
Figure 4:
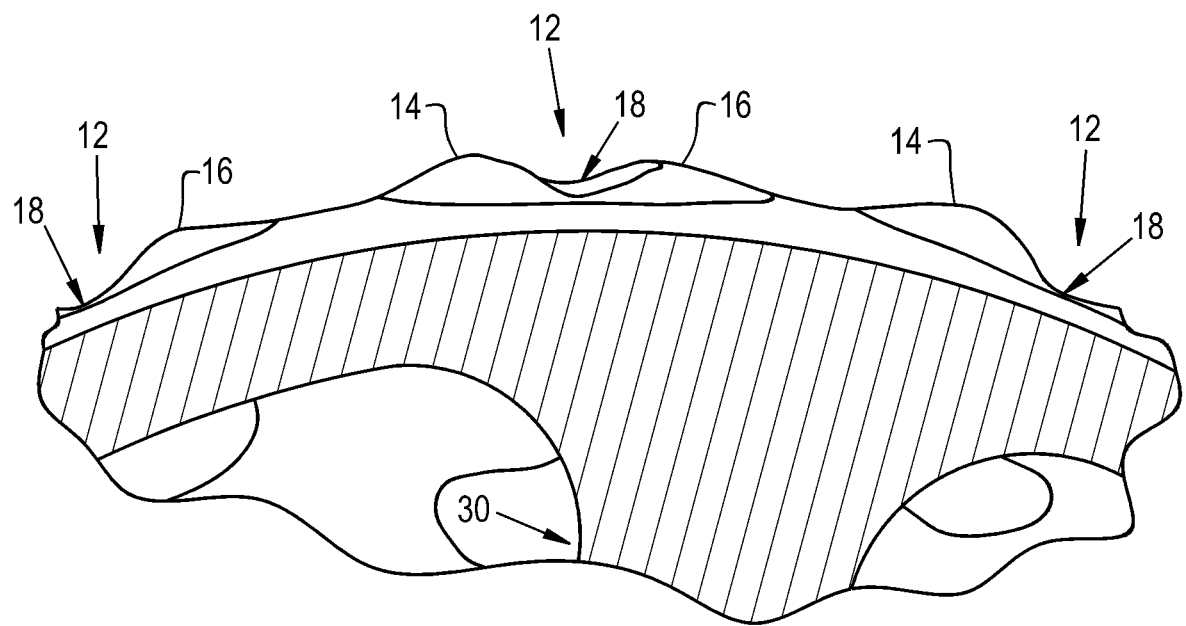
FIG. 4 is another perspective view of the reamer illustrated in FIGS. 1-3.

Referring now to the drawings, and more particularly to FIG. 1, there is shown a portion of an orthopaedic reamer 10 that includes a shell 20 and a cutting tooth arrangement 12 formed in the shell 20. The shell 20 may be, for example, a hemispherical shell comprising a metal, such as stainless steel, that is sized and configured to rotate within a joint to remove damaged tissue, such as bone tissue. The cutting tooth arrangement 12 includes a cutting tooth 14 and a feature 16 which controls the depth-of-cut that the cutting tooth 14 can take. By controlling the depth of cut of the teeth of the reamer 10, the reaming experience can be customized for the best balance of sharpness and aggressiveness. FIGS. 1 and 2 only illustrate a single cutting tooth arrangement 12, but it will be appreciated that the reamer 10 may include a plurality of cutting tooth arrangements, some or all of which are likely identically configured, as illustrated in FIGS. 3-4.

In the illustrated embodiment, the depth-of-cut feature 16 is configured as a "skid" which is formed into the geometry of the cutting tooth arrangement 12. In some embodiments, the cutting tooth 14 and the skid 16 both extend outwardly from a surface 17 of the shell 20. The amount of cut that the cutting tooth 14 can take is easily customized by altering the design of the tools which form the cutting tooth 14 and the skid 16. The cutting tooth 14 has a predefined profile with a cutting edge 15 having a cutting depth D. The skid 16 is positioned forward of the cutting tooth 14, relative to a direction of movement DM of the shell 20 at the location of the cutting tooth 14. The skid 16 defines a control depth A, which controls a cutting depth of the cutting tooth 14 during surgery. The control depth A may be equal to a distance between a peak 22 of the skid 16 and a peak 24 of the cutting tooth 14, with the skid 16 acting to space the cutting edge 15 from the surface being reamed, e.g., a joint surface.

In the embodiment shown, the cutting tooth arrangement 10 includes a hole 18 through the metal shell 20 that is round. In other embodiments, the hole 18 can be differently configured, such as oval, square, rectangular, D shaped, or have 2 flat sides or 2 oval sides. Regardless of the specific configuration, the skid 16 will be located on the side of the hole 18 opposite from the cutting tooth 14. The skid 16 may include an edge 26 that faces the cutting edge 15 of the cutting tooth 14, with the cutting edge 15 facing forwardly. By facing the edge 26 of the skid 16 toward the cutting edge 15 of the cutting tooth 14, the skid 16 will not tend to cut through bone or other tissue during forward movement of the reamer 20. Further, the cutting tooth 14 may define a tooth length TL and the skid 16 may define a length L that is less than the tooth length TL, as illustrated in FIG. 2, so the peak 22 of the skid 16 is lower than the peak 24 of the cutting tooth 14 when the skid 16 and the cutting tooth 14 extend at the same angle relative to the shell 20.

The present invention provides the surgeon with the most accurate ream possible. This is achieved by combining a cutting tooth 14 that is known to cut a smooth, accurate cavity with a skid (i.e., depth control feature) 16 to control the depth of cut resulting in improved surgeon "feel".

Some acetabular reamers use radiused teeth to provide a smooth cutting feel. Radiused teeth tend to leave a grooved cavity which is not optimum. Other known reamer designs have added chip breakers to teeth to attempt to overcome aggressiveness. This has not been effective and adds features which can build up chips during use.

Although the depth-of-cut feature 16 is shown and described as a skid, it is possible that it could be differently configured. For example, the depth-of-cut feature 16 can be configured as a raised bump or any other suitable surface ahead of the cutting tooth 14, as long as it provides a controllable cutting depth D based on the selected distance A of the depth-of-cut feature 16.

Adding the skid 16 to each cutting tooth 14 may cause more deformation in the dome of the drawn shell 20 than the same tooth style without the skid. This variation in the deformation of the shell can be accommodated if it occurs.

Referring specifically now to FIGS. 3-4, the reamer 10 is illustrated in perspective view to show multiple cutting tooth arrangements 12 formed in the shell 20. Each of the cutting tooth arrangements 12 may be substantially identically configured, i.e., the geometry of the cutting tooth 14 and the skid 16 of each arrangement 12 may be the same. The spacing between adjacent cutting tooth arrangements 12 may be varied across the surface 17 of the shell 20 so, for example, the cutting tooth arrangements 12 are not evenly spaced about the shell 20. To connect the reamer 10 to a driver, such as a rotary drill, a driver connector 30 may be disposed within the shell 20. The driver connector 30 may be any type of configuration that is suitable for connecting to a driver that will rotate the reamer 10. Exemplary driver connectors that may be incorporated in the reamer 10 are the Othy style connector and the Precimed style connector, as described by U.S. Pat. No. 10,092,301 to Weekes et al., the entirety of which is incorporated herein by reference.

While this invention has been described with respect to at least one embodiment, the present invention can be further modified within the spirit and scope of this disclosure. This application is therefore intended to cover any variations, uses, or adaptations of the invention using its general principles. Further, this application is intended to cover such departures from the present disclosure as come within known or customary practice in the art to which this invention pertains and which fall within the limits of the appended claims.

What is claimed is:

1. An orthopaedic reamer, comprising: a shell; and at least one cutting tooth arrangement formed in the shell, the at least one cutting tooth arrangement including: a cutting tooth having a predefined profile with a cutting edge having a cutting depth; and a depth-of-cut feature positioned forward of the cutting tooth, relative to a direction of movement of the shell at the location of the cutting tooth, the depth-of-cut feature having a control depth which controls a cutting depth of the cutting tooth during surgery, wherein the cutting tooth and the depth-of-cut feature both extend outwardly from a surface of the shell.

2. The orthopaedic reamer of claim 1, wherein the depth-of-cut feature is configured as a skid.

3. The orthopaedic reamer of claim 1, wherein the at least one cutting tooth arrangement comprises a plurality of the cutting tooth arrangements formed in the shell, each of the cutting tooth arrangements being substantially identically configured.

4. The orthopaedic reamer of claim 1, wherein the shell defines a hole therethrough, the cutting tooth being located on a first side of the hole and the depth-of-cut feature being on a second side of the hole that is opposite the first side.

5. The orthopaedic reamer of claim 4, wherein the cutting edge faces forwardly and the depth-of-cut feature includes an edge facing the cutting edge.

6. The orthopaedic reamer of claim 4, wherein the hole is round.

7. The orthopaedic reamer of claim 1, wherein the cutting tooth defines a tooth length and the depth-of-cut feature defines a length that is less than the tooth length.

8. The orthopaedic reamer of claim 1, further comprising a driver connector disposed in the shell.

9. The orthopaedic reamer of claim 1, wherein the shell is a hemispherical shell.

10. The orthopaedic reamer of claim 1, wherein the shell comprises a metal.

\* \* \* \* \*

UNITED STATES PATENT AND TRADEMARK OFFICE
CERTIFICATE OF CORRECTION

PATENT NO. : 11,033,282 B2
APPLICATION NO. : 16/280328
DATED : June 15, 2021
INVENTOR(S) : Todd A. Wolford et al.

It is certified that error appears in the above-identified patent and that said Letters Patent is hereby corrected as shown below:

In the Specification

Column 3
At Lines 23 and 24, please delete "distance A", and substitute therefore --distance $\Delta$--.

Signed and Sealed this
Twenty-eighth Day of February, 2023

*Katherine Kelly Vidal*

Katherine Kelly Vidal
*Director of the United States Patent and Trademark Office*